United States Patent [19]

Dilley et al.

[11] 4,414,839

[45] Nov. 15, 1983

[54] GAS SENSING APPARATUS AND METHOD

[75] Inventors: David R. Dilley, East Lansing; Julian J. L. Lee, Lansing, both of Mich.; Mikal E. Saltveit, Jr., Raleigh, N.C.

[73] Assignee: Board of Trustees, a Constitutional corporation operating Michigan State University, East Lansing, Mich.

[21] Appl. No.: 198,113

[22] Filed: Oct. 17, 1980

Related U.S. Application Data

[63] Continuation-in-part of Ser. No. 29,293, Apr. 12, 1979, abandoned.

[51] Int. Cl.³ .............................................. G01N 27/12
[52] U.S. Cl. ......................................... 73/23; 73/23.1; 422/98
[58] Field of Search .......................... 73/23, 23.1, 27 R; 338/34; 422/98; 324/71 SN; 340/634

[56] References Cited

U.S. PATENT DOCUMENTS

| | | | |
|---|---|---|---|
| 2,965,842 | 12/1960 | Jacobson | 324/71 SN |
| 3,097,518 | 7/1963 | Taylor et al. | 73/27 R |
| 3,097,520 | 7/1963 | Thompson | 73/27 R |
| 3,603,134 | 9/1971 | Norem | 73/27 R |
| 3,660,034 | 2/1972 | Baranyi et al. | 73/19 |
| 4,012,692 | 3/1977 | Eicker | 324/71 SN |
| 4,226,112 | 10/1980 | Jibelian | 73/23.1 |
| 4,250,737 | 2/1981 | Biglin | 73/23 |

OTHER PUBLICATIONS

Figaro Engineering Ltd., "Figaro Gas Sensor TGS", pp. 1 and 2, May 1, 1976.
S. P. Burg et al., "A High Sensitive Katharometer and Its Application to the Measurement of Ethylene".
T. Seiyama et al., "A New Detector for Gaseous Components Using Semiconductive Thin Films", *Analytical Chemistry*, vol. 34, No. 11, pp. 1502–1503, Oct. 1962.
K. A. Ramsteiner et al., "Simple Method for Gas Chromatographic Determination of Ethylene Emitted From Plant Tissue", *Analytical Chem.*, vol. 46, No. 11, pp. 1621–1622, Sep. 1974.
L. H. Hamilton, *Application of Fisher Model 25 Gas Partitioner to Respiratory and Blood Gas Determinations*, pp. 1–14, Aug. 1961.

*Primary Examiner*—Stephen A. Kreitman
*Attorney, Agent, or Firm*—Ian C. McLeod

[57] ABSTRACT

A sensing apparatus and method for qualitatively and quantitatively analyzing small amounts of selected oxidizable gases in a carrier gas including the associated electronic circuitry is described. The apparatus preferably includes two semi-conductor type sensing elements in electrical parallel so that the difference in resistance of the two sensors can be detected, which can be of the N or P type and which decrease or increase in electrical resistance as a function of the concentration of an oxidizable gas. Also, a method for determining fruit maturity and ripeness by the detection of ethylene in the internal atmosphere of a fruit is described which preferably uses the apparatus with the semi-conductor type sensing elements, but can use other variable resistance type gas sensing means.

15 Claims, 7 Drawing Figures

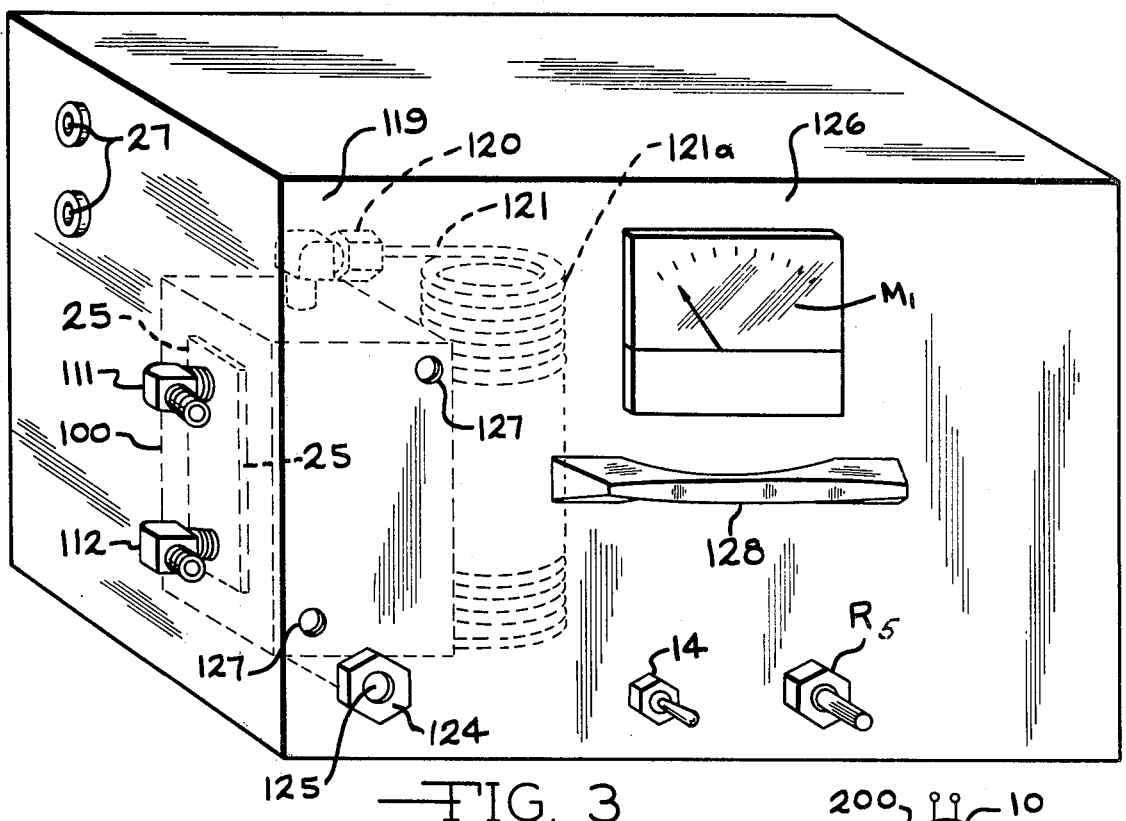
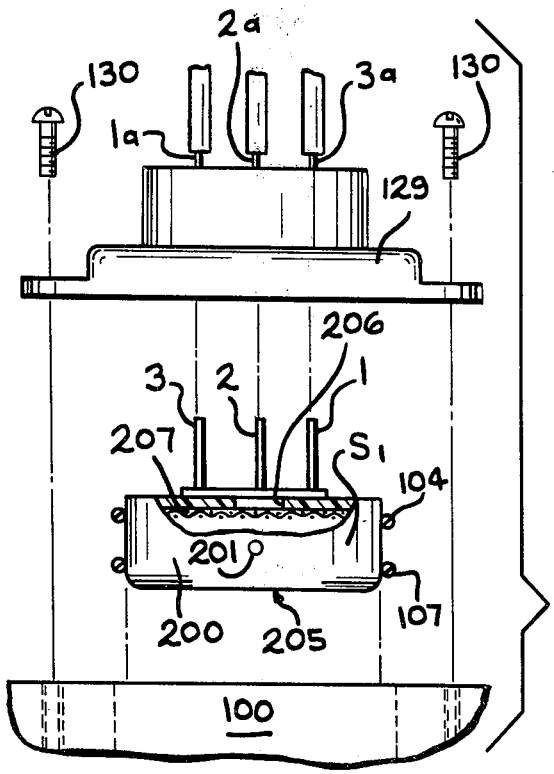
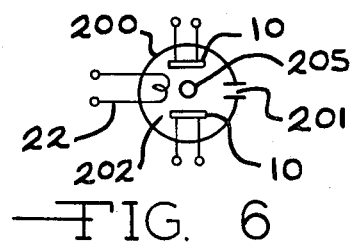
FIG. 6
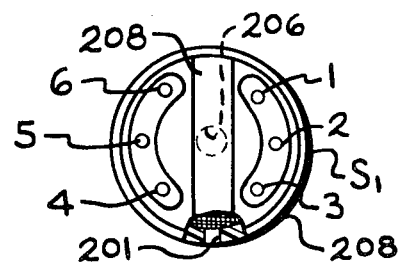
FIG. 5
FIG. 3
FIG. 4

GAS SENSING APPARATUS AND METHOD

This application is a continuation-in-part of application Ser. No. 29,293, filed Apr. 12, 1979, which is now abandoned.

SUMMARY OF THE INVENTION

The present invention relates to a gas sensing apparatus and method for qualitatively and quantitatively analyzing small amounts of selected oxidizable gases in a carrier gas, particularly a method for the detection of fruit maturity and ripeness using ethylene in the internal atmosphere of the fruit as a measure. In particular, an apparatus and method is described using a N or P type semi-conductor sensing element.

PRIOR ART

The prior art has described many different types of gas sensing means. The present invention is concerned with those sensing means having sensing elements which increase or decrease in electrical resistance as a function of the concentration of small amounts of oxidizable gases in a carrier gas, usually in amounts much less than one percent (1%) by volume.

The patent art contains detailed descriptions of variable resistance type sensing means, particularly those having N or P semi-conductor type elements. Included are U.S. Pat. No. 3,051,895 to Carson; U.S. Pat. Nos. 3,603,954, 3,625,756, 3,631,436, 3,695,848, 3,644,795, 3,835,529 and 3,900,815 all issued to Taguchi; U.S. Pat. No. 3,997,837 to Betz et al; U.S. Pat. No. 4,123,225 to Jones et al; U.S. Pat. No. 4,045,177 to McNally and U.S. Pat. No. 4,129,030 to Dolan. Literature includes articles by Mallard et al, Analytical Chemistry, Vol. 49, pages 1275 to 1277 (July 1977), and by Lewart, Popular Electronics, pages 46 and 47 (August, 1976). Also, commercially available gas sensing devices of the N semi-conductor type are described in literature of Figaro Engineering Lt of Osaka, Japan (May 1, 1976) and are preferred for the purposes of the present invention because of the linearity of decrease in resistance as a function of increasing amounts of oxidizable gases and their sensitivity when used in accordance with the present invention.

In the growing of fruits, such as apples, it is a difficult problem to determine when the fruit should be harvested so that it can be stored without excessive ripening and deterioration in storage. Thus the decisions of when to harvest a particular block of apples and how and for how long to store them, are among the most important management decisions made by the fruit grower and storage operator. High quality apples depend upon harvesting them within a certain specified period in relation to how and when the fruits are marketed. For optimum eating quality, apples marketed during the harvest season should be allowed to remain on the tree until nearly ripe. However, practical and widely recognized economic reasons largely rule this out. Fruits for refrigerated and short-term controlled atmosphere (CA) storage of 4 to 6 months should be harvested and stored after ripening has begun but prior to their attaining full eating quality. Ideally, fruits destined for CA-storage periods of 7 to 9 months or longer should be harvested and stored slightly before or just after the ripening process has begun. Storageability is inversely proportional to the degree of ripeness at harvest. Additionally, certain physiological disorders which develop in storage show a relationship to fruit ripeness at harvest. Generally speaking, apples harvested 7 to 10 days or more before they have attained full maturity are susceptible to scald and bitter pit and are prone to shrivel. Furthermore, the apples are likely to be of low dessert quality from the standpoint of color, flavor and texture. Fruit size is also sacrificed by harvesting too early. However, apples harvested after attaining full ripeness on the tree are subject to physiological disorders such as core browning, internal breakdown, mealiness and Jonathan spot, which are associated with senescence. Moreover, ripe fruit are prone to bruising and decay. Recognition of the stage of ripeness of apples after harvest is therefore more important than it is before harvest. The potential storage life of the fruit is largely determined at the moment the fruit are removed from the tree. Delays in cooling and other improper handling procedures further reduce the postharvest life.

The harvesting guidelines outlined above appear to be simple and straightforward. However, while most people can recognize a "green" or unripe apple and one that is ripe, no one can tell, without the use of elaborate electronic equipment precisely when ripening is initiated.

It is possible to estimate the optimum apple harvest dates for CA storage in various areas. Michigan and other states have similar programs in operation. Date of full bloom and temperature during the growing season are used. Predictive methods are of value, but it is important to be able to ascertain the actual progress of fruit maturation and ripening by objective means.

Examination of the fundamental changes that occur in apples as they mature and ripen on the tree reveals that a number of physiological processes proceed culminating in several readily observable characteristics. These include softening of the flesh, loss of chlorophyll, increase in carotenoid and anthocyanin pigments, conversion of starch to sugars, decrease in acidity and astringency and an increase in juiciness, flavor and aroma. These processes are brought about through qualitative and quantitative changes in metabolism. Qualitative, in that new biochemical pathways are initiated and quantitative, vis a vis a several-fold increase in the rate of metabolism. Ethylene is the underlying factor responsible for initiating the ripening process.

Ethylene is a gaseous plant hormone that causes fruits to ripen. It is produced at a low and fairly constant rate as fruits develop on the tree. This low rate of production normally persists through the last few weeks of development unless the fruits are perturbed by some environmental or chemical stress. The ethylene production rate then increases abruptly signalling the initiation of the ripening process, which culminates in the biophysical and biochemical changes noted earlier. The change in ethylene production rate is immense in proportion to the low steady-state rate typical of immature fruit; and over the course of 7 to 10 days, causes the internal atmosphere concentration to increase from about 0.1 ppm to 10 or 100 ppm. This rapid increase in ethylene concentration follows a predictable time course in which the logarithm of the ethylene concentration increases linearly with time reaching a maximum when the apple is fully ripe. This rapid increase in ethylene production is termed "autocatalytic" and is a prerequisite for fruit ripening.

Determination of the low ethylene levels (e.g. 0.1 ppm) within immature fruits requires a very sensitive and elaborate gas chromatograph in the laboratory. However, detection of higher ethylene levels (e.g. 0.5 ppm or higher) as fruits begin to ripen can be accomplished with less elaborate equipment. Several years ago, the inventors developed a modification of the Kitagawa colorimetric procedure for measuring ethylene and adapted it for use by fruit storage operators to assess fruit maturity and determine storageability of different lots of apples. This procedure entailed extracting the internal gaseous atmosphere from a bulk sample of 15 to 20 apples and analyzing the ethylene colorimetrically. A chemical in the indicator tube changes color from yellow to blue as it reacts with ethylene. The indicator tubes can detect an ethylene concentration of 0.5 ppm or greater in a 200 ml gas sample. About 15 minutes is required for each sample. The glassware and equipment costs about $200 and the indicator tubes about $1 each. Several fruit storage operators are equipped for this analysis. It is expensive and not sensitive enough. Ethylene causes ripening of other fleshy fruits.

What is needed by the art is a relatively inexpensive, portable gas sensing apparatus and method. Such a device would also be useful to monitor ethylene evolved from the fruit or added to the atmosphere in fruit storages. Such detection apparatus using variable resistance type sensing elements which are affected by oxidizable gases would also be useful as a detector for ethyl alcohol in sobriety tests; to detect ammonia leaks in refrigeration systems; carbon monoxide and methane in mines; engine exhausts; and furnace stack emissions; and in any other setting where it is desired to know the presence and/or concentration of a small amount of an oxidizable gas in a carrier gas.

OBJECTS

It is therefore an object of the present invention to provide a gas detector apparatus and method for determining the presence of and the concentration of selected oxidizable gases in a carrier gas. It is further an object of the present invention to provide an apparatus and method for determining the maturity and ripeness of fruits. Further still, it is an object of the present invention to provide an apparatus which is portable, relatively inexpensive and simple to use in the field, such as an orchard, warehouse storage, or in a vehicle. Further, it is an object of the present invention to provide an apparatus which is useful in teaching and research. These and other objects will become increasingly apparent by reference to the following description and to the drawings.

IN THE DRAWINGS

FIG. 3 is a front perspective view of the gas manifold mounting block and column of FIG. 2 installed in a portable housing.

FIG. 4 is a front view of sensor S1 and a miniature 7-pin socket which presses onto terminals on the gas sensor S1 (or S2).

FIG. 5 is a plan view showing a commercial gas sensor S1 or S2 adapted to provide gas flow across the sensing element mounted in a tube or housing with a hole on the side of the tube as also shown in FIG. 2.

FIG. 6 is a schematic view of the sensor S1 or S2.

GENERAL DESCRIPTION OF THE INVENTION

Figure 1:
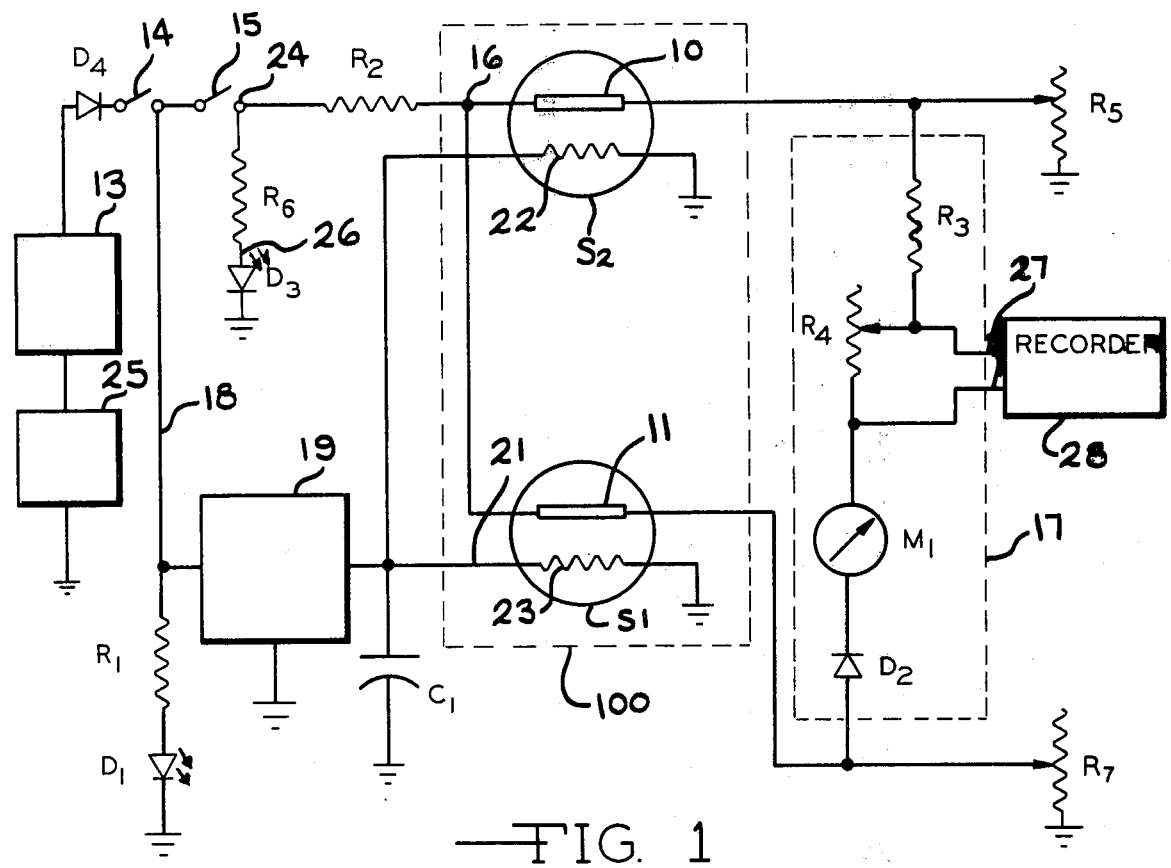
FIG. 1 is an electrical diagram showing the preferred circuit of the present invention utilizing N-type semiconductor elements in two gas sensors S1 and S2 in electrical parallel so that the difference in resistance of the two sensors can be detected and which can be used to determine the presence and the concentration of small amounts of an oxidizing gas in a carrier gas.

The present invention relates to an electrically powered oxidizable gas detector apparatus which comprises at least two gas sensor means each having a sensing element which decreases or increases resistance as a function of the adsorption of oxidizable gases in a carrier gas on the sensing elements in a parallel electronic circuit so that the difference in resistance of the two sensing elements can be detected when powered by a direct current power source, wherein the difference in resistance of the sensing elements is a function of the increasing concentration of the oxidizable gases and is detected by the electronic circuit and wherein one sensor element is adapted to be used for a reference gas and the other for an unknown oxidizable gas; electrical heater means adjacent to each sensing element to provide an operating temperature and powered in parallel by the direct current source and controlled by a voltage regulator means to maintain a constant voltage to each heater means; and detection means in conjunction with the sensing elements for detecting the difference in resistance between the sensing element for the reference sensing element and the other sensing element when there is a difference in composition of gaseous oxidizable compounds in the gases supplied to the two sensing means. The usual reference gas, air is also the carrier gas.

In particular, the present invention relates to the improvement in an electrical detector apparatus which comprises an electrically powered gas sensor means in an electronic circuit with a heating element to supply an operating temperature to at least one sensing element adjacent thereto wherein the sensing element decreases or increases in resistance upon exposure to an oxidizable gas in a carrier gas, wherein the amount of decrease or increase in resistance of the sensing element is a function of the increasing concentration of the oxidizable gas and is detected by detection means in the electronic circuit and wherein the sensing element is mounted inside a tube as a sensor housing with openings for inlet and exhaust of gases adjacent the sensing element wherein the tube is closed at at least one end and has a small hole as one opening through the side of the tube adjacent the sensing element; a gas manifold mounting block made of a heat conductive material, metal, for example, to act as a heat sink having an opening adapted to receive the tube in closely spaced relation and having a first conduit leading to the hole in the side of the tube and a second conduit through the mounting block adjacent the other opening in the tube; and seal means between the opening in the gas manifold mounting block and the gas sensor tube to prevent gas leakage from the space between the tube and the gas manifold mounting block and to provide a flow of the gases through the openings and in the tube across the sensing element. The hole in the sensor means tube is preferably between about 1 and 2 mm in average diameter and is positioned such that the gas is directed on the sensing element.

The improved gas sensing apparatus particularly increases the sensitivity of standard N semi-conductor type sensing elements, particularly those made of sintered tin oxide, by several multiples of 10 on a reproducible basis which is a very unexpected result. The tin oxide elements have a usual sensing range of above about 0.01 percent or 100 parts per million of an oxidizing gas in a carrier gas. This sensitivity is increased by the apparatus of the present invention to down to about 0.2 parts per million. The P type semi-conductor type elements are also useful.

The present invention generally relates to the method for determining the difference in concentration of small amounts of oxidizable gases in a carrier gas which comprises: providing at least two gas sensor means each having a heated sensing element which decreases or increases resistance and thus increases or decreases current output at a constant voltage as a function of the increasing adsorption of small amounts of gaseous oxidizable compounds in a carrier gas on the elements in a parallel electronic circuit with a detection means so that the difference in resistance between the two sensing elements can be detected and is powered by a direct current power source, wherein one sensor element is for detecting a reference gas and the other for detecting an oxidizable gas in a reference gas; and introducing the gases to the sensing elements in the sensor means and determining the difference in resistance as current output from the sensing elements with the detection means.

The present invention also relates to the method for determining the concentration of small amounts of oxidizable gases in a carrier gas which comprises providing at least two gas sensor means each having a heated sensing element which decreases or increases resistance and thus increases or decreases current output at a constant voltage as a function of the increasing adsorption of small amounts of gaseous oxidizable compounds in a carrier gas on the sensing element in a parallel electronic circuit so that the difference in resistance between the two sensing elements can be detected and is powered by a direct current power source, wherein the sensor means are connected by a conduit in a sealed flow path at opposite ends of the conduit with an upstream and a downstream sensor means; introducing a reference gas through the upstream sensor means and providing an oxidizable gas in a reference gas in the conduit adjacent the upstream sensor means such that the downstream sensor means detects the concentration of the oxidizable gas as it flows across the element and provides a response from the electronic circuit which is proportional to the concentration of the oxidizable gas. The conduit is preferably filled with an adsorptive or absorptive material for selected oxidizable gas or gases. Such materials include activated alumina, silica gel and other commercially available column packing gas chromatographic materials. Such materials provide a separation in time of multiple compounds in a carrier gas.

The present invention particularly relates to the method for determining fleshy fruit maturity and ripeness particularly prior to harvest, after harvest, or during storage which comprises providing an electrically powered gas sensor means which decreases or increases resistance upon contact with an oxidizable gas in air, wherein the amount of decrease or increase in resistance of the sensing element is a function of the increasing concentration of the oxidizable gas, such as ethylene, and is detected by an electronic circuit whose current output is a function of the difference in resistance of the sensing elements; selecting an immature fleshy fruit and a maturing fleshy fruit of the same species with air in the internal atmosphere of the fruits which contains increasing concentrations of at least one specific oxidizable gas as a result of maturation and ripening; and separately introducing air samples removed from the internal atmosphere of the immature fruit and the maturing fruit of the same species across the gas sensing element and determining the difference in the current output from the electronic circuit, whereby as the maturing fruit begins to ripen the concentration of the specific oxidizable compound, such as ethylene, increases indicating that fruit ripening processes are proceeding and that the fruit is becoming ripe and wherein the remaining oxidizable compounds in the air samples remain relatively constant as between the maturing and immature fruits. Other oxidizable compounds are formed in fruits as ripening proceeds but usually only after the ethylene concentration has reached levels readily detectable by the apparatus described herein.

SPECIFIC DESCRIPTION

Referring to the electrical circuit of FIG. 1, sensors S1 and S2 with N type semi-conductor sensing elements 10 and 11 are shown connected in electrical parallel. The elements are powered by a 12.6 volt battery 13 (or from an AC to DC regulated power supply) having the positive terminal leading to the sensing elements 10 and 11 through a diode D4 (which protects the circuit from reverse current flow), miniature single pole, single throw switches 14 and 15 and resistance R2 to the junction 16 between the elements 10 and 11. The other side of the elements 10 and 11 is connected to adjustable resistances R5 and R7, respectively, which are each connected to ground G. A detector means 17 shown by broken lines forms an electrical bridge between resistances R5 and R7 and the sensors 10 and 11. Thus the basic circuit is similar to a Wheatstone bridge which is well known to those skilled in the art.

The detector means 17 (shown in broken lines) includes a fixed resistor R3, variable resistance R4, a microammeter M1 and a diode D2 to limit the direction of current flow. The resistance R3 protects against overload of the meter M1 and R4 provides a means for adjusting output to external recorder means. Between the switches 14 and 15, a lead 18 is provided through resistance R1 through light emitting diode D1 to ground G which detects current flow to the voltage regulator 19 through lead 18. The voltage regulator 19 is provided with common outlet leads 20 and 21 to heater elements 22 and 23 for sensing elements 10 and 11 which are in turn connected to ground G. The controlled voltage from the voltage regulator 19 is necessary to provide a controlled uniform heating of the elements 10 and 11. A capacitor C1 is provided between ground G and leads 20 and 21 to smooth any minor voltage surges from the regulator 19. At point 24 a lead 26 to ground is provided through a light emitting diode D3 to indicate that power is being supplied to the sensing elements 10 and 11. A heater 25 connected to ground is provided for heating the gas manifold mounting block 100 (shown in dotted lines in FIG. 1) for the sensors 10 and 11. Terminals 27 are provided for a recorder means 28 which can be used in addition to meter M1.

Figure 2:
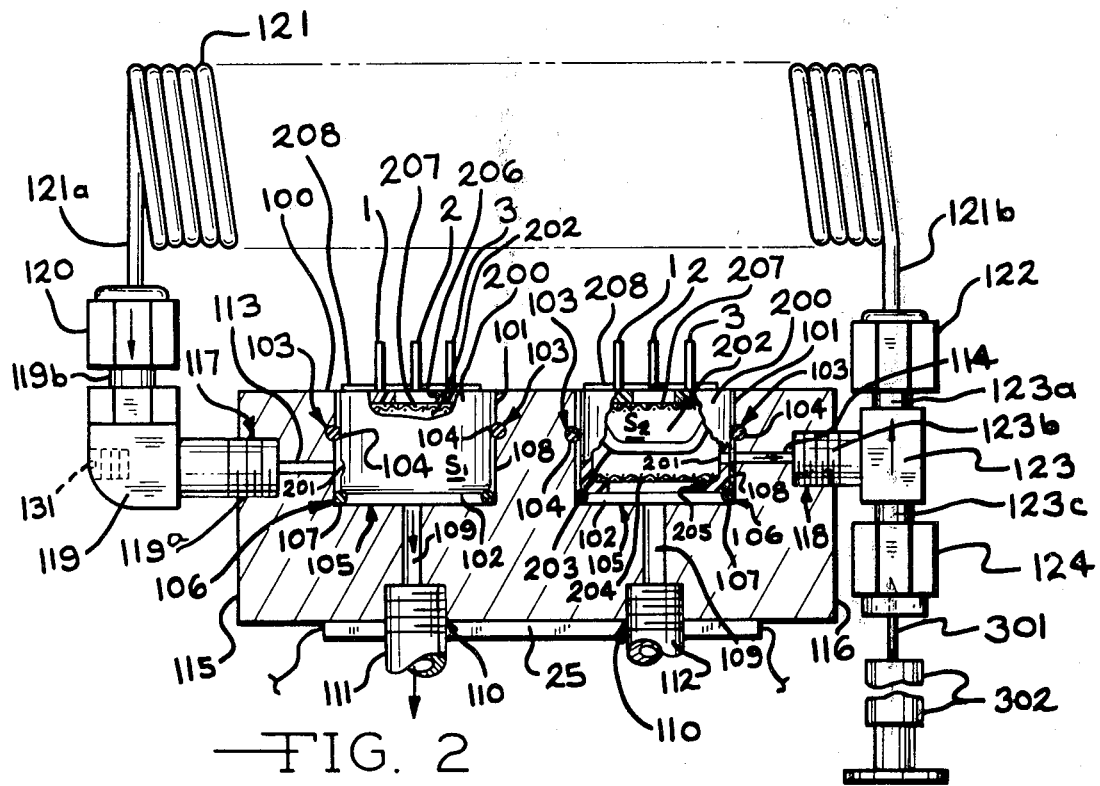
FIG. 2 is a front partial cross-sectional view of the apparatus of the present invention, particularly illustrating an adsorption or absorption gas chromatography column between N-type semi-conducting elements in sensors S1 and S2 in a gas manifold mounting block which also acts as a heat sink.

Referring to FIG. 2, the gas manifold block 100 is made of metal, preferably brass, to provide a common heat sink for the sensor means S1 and S2. This construction is important to the reliability and sensitivity of the measurements. The gas manifold mounting block 100 is preferably heated by external heater 25 to a fixed temperature, normally between about 20° and 50° C., preferably 35° C. Since the apparatus is to be portable and used in all sorts of environments the heater 25 is important.

Both sides of the block 100 as shown in FIG. 2 have a number of elements in common. The block 100 is provided with two (2) cylindrical holes 101 for close fitting of the sensors S1 and S2 with grooves 103 midway into the holes 101 supporting ring seals 104. At the bottoms 105 of the holes 101, seats 106 are provided with ring seals 107. Between the seals 104 and 107 and the sensors S1 and S2 are annular sealed spaces 108. Spaces 102 are also provided between the sensors S1 and S2 and the bottom of the holes 101. The gas manifold mounting block 100 is provided with holes 109 concentric with the longitudinal axis of the holes 101 leading to the bottoms 105 of the holes 101. The holes 109 are provided with threaded openings 110. An outlet fitting 111 is provided in one of the openings 110 and an inlet fitting 112 is provided on the other opening 110.

Perpendicular to the axis of the holes 101 are provided holes 113 and 114 from opposite sides 115 and 116 of the gas manifold mounting block 100. These holes 113 and 114 are provided with threaded openings 117 and 118 which are concentric with the holes 113 and 114. The holes 113 and 114 with openings 117 and 118 are mirror images of each other. At one end 115 of the gas manifold mounting block 100, is a right angle elbow 119 with one end 119a threaded into hole 117. The other threaded end 119b is fitted with a nut 120 mounted on an extension 121a of a flanged tube 121 to provide a gas sealed connection to the elbow 119. The tube 121 is in the form of a helical coil with a second flanged extension 121b fitted to a second nut 122 attached to a threaded extension 123a of a T 123 having a leg 123b threaded into the opening 118 in the block 100. The tube 121 is filled with an oxidizable gas adsorptive or absorptive material and acts as a gas chromatography column. A threaded inlet leg 123c is fitted with a nut 124 having a sealed septum 125 (FIG. 3) which is penetrable by a syringe 300 and needle 301 which is an injection method well known to those skilled in the art. As seen in FIG. 3, the gas manifold block 100 is mounted in a housing 126 by means of screws 127. A handle 128 is provided on the housing 126 for carrying. The output terminals 27 from the detection means 17 can be fed to a recorder 28 or other device.

The details of the construction of the preferred gas sensor S1 and S2 which are identical are shown in FIGS. 2, 4, 5 and 6. A hollow cylindrical housing or tube 200 made of an inert plastic is provided with a small hole 201 leading to the space 108. The housing 200 has a hollow interior 202 in which is mounted a N-type gas sensing element 203 which is schematically shown as sensing element 10 or 11 in FIGS. 1 and 6. The hole 201 is adjacent the sensing element 203. A screen 204 and opening 205 are provided on one side of the sensor S1 and S2. The sensors S1 and S2 have a second opening 206 covered by a screen 207. This is the conventional construction of a Taguchi type gas sensor (TGS) except for the hole 201 which is important for flow direction of the oxidizable gases across the elements 10 and 11. The elements S1 and S2 have a strip 208 closing the opening 206. The opening 206 is sealed with the metal strip 208 using an epoxy resin bonding agent or the like. The openings 201 of the sensors S1 and S2 are connected to holes 113 and 114. The sensors S1 and S2 shown in FIGS. 2, 4, 5 and 6 are a Taguchi Gas Sensor Figaro 812. The important aspect of the modification is the flow path of the gas across the sensing element 203.

FIG. 4 shows a conventional miniature 7-pin socket 129 which bolts to the block 100 by means of bolts 130. The leads 1a, 2a and 3a correspond to terminals 1, 2 and 3. The terminals 1 to 6 project from the sensor housing 200 and are electrically connected as shown in FIG. 6. Only two of the terminals 1 and 4 or 3 and 6 are connected into the circuit as shown in FIG. 1.

Table 1 shows the functional characteristics of the Figaro$_{TM}$ Sensor No. 812

TABLE 1

| | |
|---|---|
| Heater Volts | 5.0 ± 0.2V |
| Heater Power Consumption | 620 mW |
| R$_{(IB\ 1000)}$ | 1kΩ–10kΩ |
| This represents sensor resistance when exposed to 1000 ppm isobutane in air | |
| R$_{(IB\ 3000)}$/R$_{(IB\ 1000)}$ | approx. 0.55 |
| This represents ratio of | |
| sensor resistance in 3000 ppm isobutane ; | |
| sensor resistance in 1000 ppm isobutane. | |
| Warm-up Time | within 2 minutes |

This sensor means is designed as a general purpose oxidizable gas sensor means in the concentration range between about 0.05 to 1.0 percent in a carrier gas.

Table 2 shows the elements of the preferred circuit shown in FIG. 1.

TABLE 2

| | |
|---|---|
| 1C1 | MLM 309K Regulator |
| C1 | 1μF electrolytic capacitor |
| D1&D3 | light emitting diode |
| R1, R2, R6 | 220 ohm (¼ Watt) |
| R3 | 2.2 K (¼ Watt) |
| R4 | 1 kilo ohms linear taper Pot. |
| R5 | 50 kilo ohms linear taper Pot. |
| M1 | 0–50μ Amp Meter |
| D2 | 1N904 diode |
| D4 | Mallory $_{TM}$ M2.5A diode |

The TGS gas sensors can detect:

(1) hydrocarbons and their derivatives such as: methane; ethane; propane; butane; pentane; hexane; heptane; octane; decane; petroleum ether; petroleum benzene; gasoline; kerosene; petroleum naphtha; acetylene; ethylene; propylene; butadiene; butylene; benzene; toluene; o-xylene; m-xylene and ethylene oxide;

(2) halogenized hydrocarbons such as: methyl chloride; methylene chloride; ethyl chloride; ethylene chloride; ethylidene chloride; trichloroethane; vinylidene chloride; trichloro ethylene; methyl bromide and vinyl chloride;

(3) alcohols such as: methanol; ethanol; n-propanol; iso-propanol; n-butanol and iso-butanol;

(4) ethers such as: methyl ether and ethyl ether;

(5) ketones such as: acetone and methyl ethyl ketone;

(6) esters such as: methyl acetate; ethyl acetate; n-propyl acetate; isopropyl acetate; n-butyl acetate and iso-butyl acetate;

(7) nitrogen compounds such as: nitro methane; mono methyl amine; dimethylamine; trimethylamine; mono ethylamine and diethylamine;

(8) inorganic gases such as: ammonia; carbon monoxide; hydrogen; hydrogen cyanide; hydrogen sulfide and carbon disulfide.

OPERATION

The operation of the gas sensor apparatus for the detection of ethylene in air from the internal atmosphere of a fleshy fruit is generally illustrative. Ethylene is initially present in low amounts in unripe fruits (between about 0.05 to 0.1 ppm) and increases 100 to 1000 times as it causes fruit to ripen. The problem is to detect the precise point at which the ethylene concentration increases to about 0.2 and 0.5 ppm indicating the point of maximum storability of the fruit and the ability to ripen in storage. This increase in ethylene initiates autocatalytic ethylene production and fruit ripening. As the ripening process proceeds, numerous aldehydes and ketones develop which gives the fruit the characteristic "fruit" smell and flavor. These gases can also be sensed by the apparatus of the present invention which detects oxidizable gases quantitatively down to about 0.1 to 0.2 ppm (1 to $2 \times 10^{-5}$%).

In one mode of operation of the apparatus of FIGS. 1 and 2, samples of the internal atmospheres from the fruit of an early maturing variety and a much later maturing variety at the same temperature are removed with a syringe 300 by means of a needle 301. This step compensates for humidity and thermal effects. The plug 131 and nut 124 are removed in this mode of operation. The samples are then introduced through fittings 111 and 112 across the elements 201 of sensors S1 and S2 and out through conduits 113 and 114 to the atmosphere. The later maturing variety sample is passed across S1. The "background gases", are essentially the same in both varieties and thus the early ripening variety will show a positive response for ethylene in S1 as read on the meter M1 if the fruit is beginning to ripen. Unexpectedly it has been found that this method can be used with many different early and late maturing varieties of fruits.

The use of the apparatus for apples is particularly illustrative. In ethylene detection mode of operation, preferably two 1 ml gas samples in syringes are injected simultaneously into the two sensors S1 and S2. One sample is from the fruit of questionable ethylene content and the other from the fruit of a later maturing variety with low ethylene level, which serves as a blank or control. If the gas sample in question does not contain ethylene, the detector meter M1 does not respond. If ethylene is present, the meter responds immediately and is linear from 0 to at least 10 ppm of ethylene. The analysis takes about 3 minutes per sample.

In the ethylene determination mode, a 1 ml gas sample from the fruit in question is injected in port 125 and is carried through the column 121 to sensor S2, and the analysis is complete in about 2 minutes. The meter M1 response is linear from 0 to at least 10 ppm of ethylene.

Ethylene, is quantitatively determined using the gas chromatographic column of activated alumina in tube 121 as shown in FIG. 2. This activated alumina column has an affinity for ethylene but not aldehydes, esters and alcohols. The plug 131 and nut 124 are in place as shown in FIG. 2. Thus a syringe 300 and needle 301 is used to inject a gas sample from the internal atmosphere (or seed cavity) of the maturing fruit into septum 125 so that it is inside T 123. A carrier gas, preferably air, at about 20 psig (2.4 atm) or from an aquarium type air pump (about 2 psig 1.1 atm) by using a chromatography column of appropriate resistance gives a carrier gas flow rate of about 8 to 15 ml per minute. The carrier gas is introduced into fitting 112 and across the element 203 of element S2 and then the sample is carried through tube 121 to sensor S1 where the element 201 of S1 responds by precisely decreasing in resistance as a function of the ethylene concentration. The downstream sensor S1 gas pressure is above atmospheric pressure and the upstream sensor S2 has a pressure above that of S1. The upstream sensor S2 has a pressure in space 202 which is above atmospheric and above the pressure in the space 202 in S1. The difference in resistance of sensors S1 and S2 is displayed by the meter M1. The unit is adjusted using the carrier gas, R5 and R7 to make certain the meter M1 is at a reference or "0" point. The gas chromatography tube 121 is preferably filled with activated alumina which separates ethylene from ethane, aldehydes, ketones, alcohols and esters present in the internal atmospheres of fruits. Most of these other oxidizable materials are passed through the column in about 5 seconds while ethylene is delayed for about 30 seconds to 2 minutes.

Calibration of the meter M1 response requires an accurately determined and standardized mixture of ethylene at a concentration between 5 and 10 ppm in air. Since the meter M1 response is linear with ethylene concentration, calculation of ethylene in samples is quite simple when using a fixed injection volume. A numerical factor (expressing ppm ethylene in the standard gas/meter units developed by the standard sample) is multiplied by sample meter units developed by the unknown sample, and this yields ppm of ethylene in the sample. For example, if a 1 ml sample of a 10 ppm ethylene standard gives 40 micro-amps, then the concentration of ethylene in the sample is calculated as follows:

$$\left( \frac{10 \text{ ppm ethylene in standard}}{40\mu \text{ amps for standard}} \right) \times$$

$\mu$ amps for sample = ppm ethylene

Samples of the internal atmosphere of apple fruits can be readily obtained after harvest or while the fruits are on the tree. Sampling is done by withdrawing 1 ml of gas from the internal cavity with a needle 301 (18 or 20 gauge; 1½") and syringe 300 by entering the calyx end of the apple. A clean-out wire should be used to prevent clogging of the needle 301 with tissue. A composite sample from several fruits can be obtained by employing a 10 to 20 ml syringe 300. Withdrawing a 1 ml gas sample causes a slight vacuum within the fruit, and this is equalized as air enters through the open lenticels over the fruit surface. This results in a negligible (less than 1%) dilution of the gas sample. At most this would be about 3% based on instantaneous dilution.

It will be appreciated that other resistance type sensors can be used for the fruit maturity and ripeness detection such as the catalytic detectors of the prior art. Further many different absorption or adsorption materials can be used in the gas chromatography column. Many different kinds of fruits both edible and unedible as well as flavors can be tested using the method of the present invention. Other types of detecting means can be used including recorders which trace a response on paper as a function of concentration or light emitting diodes or a digital display which respond as a function of concentration ranges. The column can be replaced by or be in series with a container or chamber or room containing the oxidizable gas to be detected and/or the source of the gas such as a fruit. Examples are: a banana ripening room, a tomato ripening room, a tobacco ripening room (ethanol to ethylene). The output of the sensors S1 and S2 can also be used to electrically regulate a control means such as a valve or a fan. The apparatus can also be used to monitor atmospheres in ethylene ripening rooms, such as for bananas, tomatoes and citrus fruits or to detect the presence of undesirable ethylene levels such as in flower warehouses or other storages or in transportation vehicles. The apparatus can also be used for onstream detection wherein the column contains a material for removal of a gas after being detected by a first detector and wherein the downstream detector indicates the absence of the removed gas by the difference in resistance from the sensors S1 and S2. All of these variations will be obvious to those skilled in the art.

Figure 7:
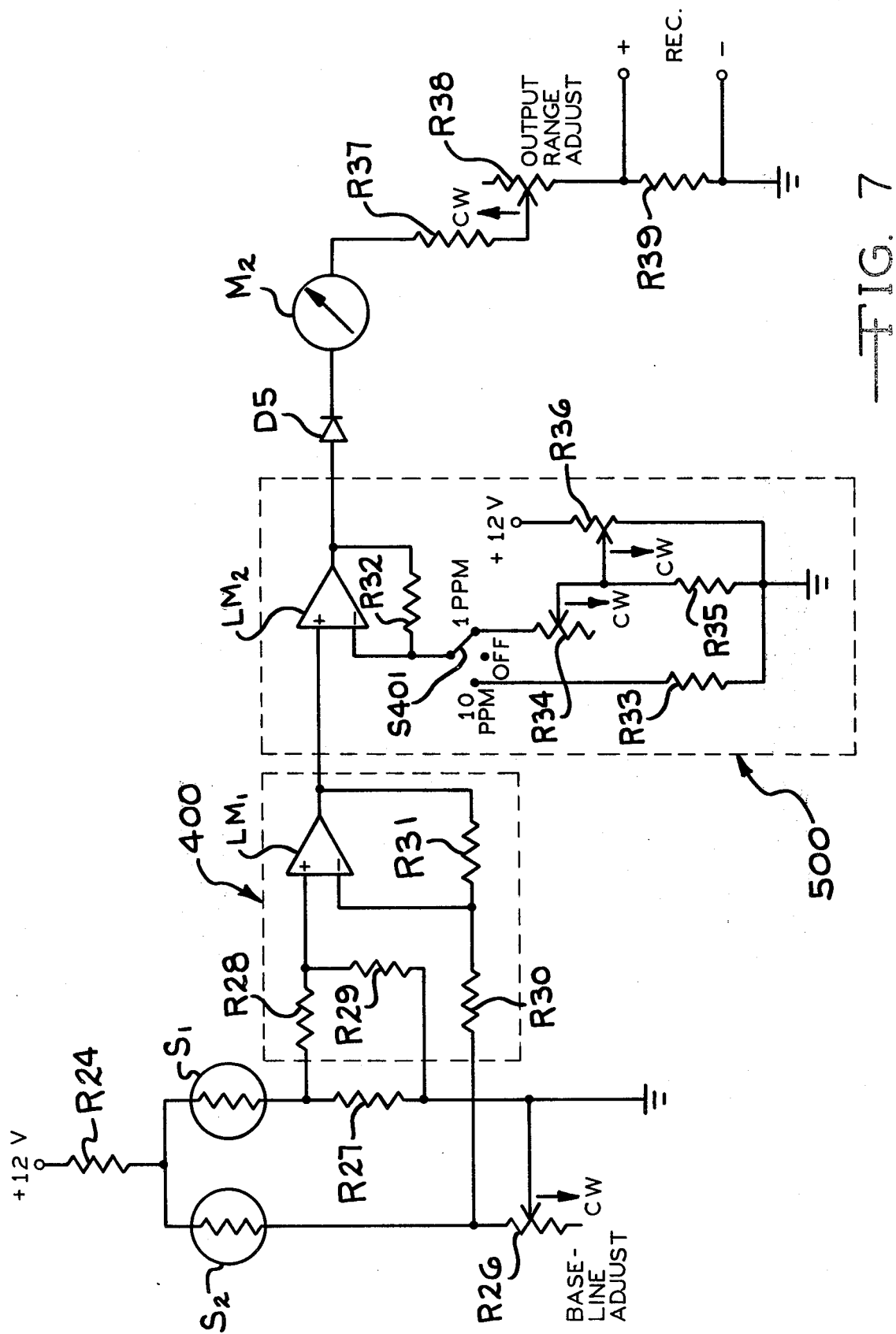
FIG. 7 is an improved detector unit including a sensor isolation circuit and a voltage amplifier circuit.

FIG. 7 shows an improved detector unit circuit including, in addition to the sensor means $S_1$ and $S_2$, a sensor isolation circuit means 400 and voltage amplifier circuit means 500. The values of the resistances "R" and the identification of other elements are shown in Table 3.

TABLE 3

| | |
|---|---|
| R24 | 2.2 kilo ohms |
| R26 | 50 kilo ohms variable |
| R27 | 43 kilo ohms |
| R28 and R29 | 22 kilo ohms |
| R30 and R31 | 1.0 megohm |
| R32 | 100 kilo ohm |
| R33 | 33 kilo ohm |
| R34 and R36 | 10 kilohm variable |
| R35 | 100 ohm |
| R37 | 2.2 kilo ohm |
| R38 10 kilo ohms variable | |
| R39 | 100 ohm |
| D5 | diode |
| LM1 and LM2 | ½LM 358 (National semiconductor) dual operational amplifier |
| Power | 12 volts DC |
| M2 | milliammeter |

$LM_1$ and $R28$ through $R31$ function as a voltage follower which isolates the sensors $S_1$ and $S_2$ from the rest of the circuits. The output of $LM_1$ is fed into $LM_2$ which functions as a linear amplifier. The gain of $LM_2$ depends on the setting of $S401$, which functions as a range selector. In the 10 ppm range, the gain of $LM_2$ is about 3.3. In the 1 ppm range, the gain of $LM_2$ is exactly 10 times that of 10 ppm range. $R_{34}$ is used to fine tune the gain of $LM_2$ at the 1 ppm range. $R_{36}$ functions as an offset adjustor which nulls the output of $LM_2$ at the 1 ppm range. The voltage output of $LM_2$ is fed to a milliammeter $M_2$ to display the response of the sensors $S_1$ and $S_2$.

The improved circuit of FIG. 7 is useful for fruit maturity and ripeness detection as described previously. It has also been found to be particularly useful for quantitative carbon monoxide detection in the circulatory or pulmonary system of mammals, particularly humans. The improved circuit will accurately detect between about 0.5 and 500 ppm of carbon monoxide.

OPERATION FOR CARBON MONOXIDE DETECTION

Carbon monoxide poisoning represents a major health problem for humans and is difficult to detect clinically and quantitatively. There has been no means for rapidly determining lung air or blood concentrations of carbon monoxide particularly under emergency conditions. Presently flame ionization detection (FID) is used by reducing carbon monoxide to methane; however, this test is difficult to perform accurately, and is expensive and time consuming. Methane may be a natural component of pulmonary air which interferes with the detection of carbon monoxide unless the gases are separated by a chromatography column.

The circuit of FIG. 7 was used with the device shown in FIG. 2 for carbon monoxide detection. Air is sampled from the lungs by breathing or forcing air from the lungs into a syringe 302 via a mouth piece and aerosol hose sampling device. Pulmonary air at the end of exhaling is used for the lung air sample since it represents the air mixture in equilibrium with the alveoli and would therefore be most reliable for carbon monoxide detection. Dried air or other carrier gas is injected through inlet tube 112 over sensor $S_2$ and then into column 121. The sample is injected through septum 125, is carried through the column 121 by the air across the active sensor $S_1$ and the ppm of carbon monoxide is read on the meter $M_2$. The column 121 contains a 5 angstrom molecular sieve which chromotographically separates oxidizable gases in the sample, particularly methane and carbon monoxide. The carbon monoxide is detected in about 3 minutes.

For blood samples for carbon monoxide detection a sample of arterial blood is obtained via a syringe and is prepared for analysis according to the procedure of Collison et al., (Blood 14(2): 162–171 1968). The blood derived gas sample is injected through septum 125, passed through column 121 and passed over the sensor $S_1$ by air which is first passed over the sensor $S_2$. The meter $M_2$ reading is translated into carbon monoxide in the blood and is expressed as cubic centimeters of carbon monoxide per 100 cubic centimeters of blood or as carboxyhemoglobin (HbCO) saturation. A normal value is about 1% HbCO for a non-smoker and about 5% HbCO for a habitual smoker. The normal range of carbon monoxide in expired air is 1 to 5 ppm for a non-smoker and is 5 to 30 ppm for smokers. Carbon monoxide poisoning produces much higher levels of 40 to 60% HbCO saturation in the blood and correspondingly higher carbon monoxide levels in the expired air. Atmospheric air commonly contains 1 to 5 ppm carbon monoxide and in high traffic areas values in excess of 50 ppm of carbon monoxide are frequently found.

We claim:
1. An electrically powered oxidizable gas detector apparatus which comprises:
  (a) at least two gas sensor means each having a sensing element which decreases or increases resistance as a function of the adsorption of gaseous oxidizable compounds in air on the sensing elements in a parallel electronic circuit so that the difference in resistance of the two sensing elements can be detected when powered by a direct current power source, wherein the difference in resistance of the sensing elements is a function of the concentration of the compounds and is detected by the electronic circuit and wherein one sensor element is adapted to be used for a reference gas and the other for an unknown oxidizable gas in the reference gas and wherein the oxidizable gas flow in at least the oxidizable gas sensor means is across the sensing element in one direction and out of the sensor means in another direction; (b) electrical heater means adjacent to each sensing element to provide a common operating temperature and powered in parallel by the direct current source and controlled by a voltage regulator means to maintain constant voltage to each heater means;

(c) detection means in conjunction with the sensing elements for detecting the difference in resistance between the sensing element for the reference sensing element and the other sensing element when there is a difference in composition of gaseous oxidizable compounds in carrier gases supplied to the two sensing means;

(d) tube means providing a sealed flow path between the sensor means to the sensing elements; and (e) inlet means in the tube means for introducing an oxidizable gas in a carrier gas between the sensing means, wherein concentrations of ethylene as the oxidizable gas in the carrier gas between 0.1 and 10 ppm can be detected by the difference in the resistance of the sensing elements.

2. The apparatus of claim 1 wherein the sensing element is a N-type semi-conductor.

3. The apparatus of claim 2 wherein the sensing element is a sintered tin oxide N-type semi-conductor.

4. The apparatus of claim 1 wherein two variable resistance means are provided in the electronic circuit for initially balancing the current output resulting from the difference in resistance of the two sensing elements while both of the sensing elements are being purged with a carrier gas.

5. The apparatus of claim 1 wherein an upstream and a downstream gas sensor means are provided at each end of a gas chromatography column in the tube means containing a selectively gas absorptive or adsorptive material with an affinity towards specific oxidizable gases such that an upstream gas sensor can be purged with air acting as a carrier gas while an unknown gas containing the oxidizable gas in the carrier gas is introduced in the inlet means between the upstream and downstream sensors in the column and then the oxidizable gas is separated from other gases on the column and then released in a short period of time and then is detected by the downstream sensor means as the carrier gas and the oxidizable gas emerge from the column.

6. The apparatus of claim 5 wherein the sensor means has a sintered tin oxide N-type semi-conductor sensing element.

7. The apparatus of claim 5 wherein the chromatographic column material adsorbs or absorbs and then releases ethylene while permitting alcohols, aldehydes and esters obtained from the internal atmosphere of fruits to pass through the column, thereby permitting qualitative and quantitative analysis of ethylene.

8. The apparatus of claim 5 wherein the gas in the sensing element in the upstream sensor means is at a pressure above that in the downstream sensor means.

9. The apparatus of claim 7 wherein at least the sensor means for the oxidizable gas in the reference gas is constructed as a tube closed at one end and open at an opposite end and containing the sensing element mounted inside the tube with a small hole adjacent the sensing element through a side of the tube such that an oxidizable gas in a carrier gas can be passed across the sensing element.

10. The apparatus of claim 9 wherein the sensor means has a sintered tin oxide N-type semi-conductor type sensing element.

11. The apparatus of claim 1 wherein the electronic circuit includes a voltage amplifier means in the circuit responsive to the current output from the sensing elements which increases the sensitivity of the detection means to the oxidizable gas.

12. In an electrical detector apparatus the improvement which comprises:

(a) at least two electrically powered gas sensor means each in an electronic circuit with a heating element to supply an operating temperature to a sensing element adjacent thereto wherein the sensing element decreases or increases in resistance upon exposure to an oxidizable gas in a carrier gas, wherein the amount of decrease or increase in resistance of the sensing element is a function of the concentration of the oxidizable gas and is detected by detection means in the electronic circuit and wherein each sensing element is mounted inside a tube as a housing for the sensor means having opposing ends, wherein the tube is closed at one end and open at the other end and has a small diameter hole as an opening for carrier and oxidizable gas inlet through a side of the tube adjacent the sensing element and wherein carrier and oxidizable gas flow is through the hole and across the sensing element and out the open end of the tube;

(b) a gas manifold mounting block made of a heat conductive material to act as a heat sink having an opening adapted to receive the tube in closely spaced relation and having a first conduit leading to the hole in the side of the tube and a second conduit through the gas manifold mounting block adjacent the open end of the tube, wherein each tube housing is mounted within the gas manifold mounting block;

(c) seal means between the opening in the gas manifold mounting block and the gas sensor tube to prevent gas leakage from the space between the tube and gas manifold mounting block and to provide a flow of the gases through the tube across the sensing element;

(d) connector means providing a sealed flow path between the first and second conduits in the mounting block and holes in the sensing means to the sensing elements; and (e) inlet means in the tube means for introducing an oxidizable gas in a carrier gas between the sensing means, wherein the concentrations of ethylene as the oxidizable gas in the carrier gas between 0.1 and 10 ppm can be detected by the difference in resistance of the sensing elements.

13. The apparatus of claim 12 wherein the tube which is the sensor housing has a cylindrical cross-section and the seal means is a ring seal adjacent the first conduit to the gas manifold mounting block opening and a ring seal adjacent the hole in the tube and second conduit such that gas can be exhausted through the block.

14. A method for determining the concentration of small amounts of carbon monoxide with other oxidizable gases in a carrier gas which comprises:

(a) providing a sealed flow path with identical P or N type semi-conductor heated sensing elements therein which decrease or increase in resistance as a function of the increasing absorption of small amounts of the carbon monoxide in a carrier stream on the sensing elements;

(b) introducing a carrier gas stream into said sealed flow path whereby the carrier gas enters a first zone containing a first one of said sensing elements in a first direction in said first zone and exits said zone of the first detector in a direction perpendicular to the direction of entry;

(c) removing said sensed carrier gas stream and injecting therein a second gas stream containing the carbon monoxide having a concentration between 0.5 and 500 ppm thereby forming a combined gas stream to be sensed;

(d) conveying said combined gas stream through a conduit which directly connects and communicates said first and second identical sensing elements and said first zone with a second zone and forms the sealed flow path, wherein the conduit contains means for separating carbon monoxide from other oxidizable gases in the combined gas stream so that carbon monoxide remains in the combined gas stream;

(e) introducing the combined gas stream into said second zone containing the second identical sensing element in a first direction;

(f) contacting the combined gas stream with said second sensing element and removing the sensed combined gas stream from said second zone along a direction perpendicular to the direction of entry;

(g) sensing the resistance of the respective sensors in the first and second zones; and (h) determining the difference in resistance of the respective sensors as a current output as an indication of the oxidizable gas to be detected, wherein concentrations of ethylene as the oxidizable component in the carrier gas between 0.1 and 10 ppm can be detected.

15. The method of claim 14 wherein the carbon monoxide is air as the carrier gas stream from the circulatory or pulmonary system of a mammal.

* * * * *